United States Patent [19]

Sanderson et al.

[11] Patent Number: 5,097,087
[45] Date of Patent: Mar. 17, 1992

[54] DIMERIZATION OF LONG-CHAIN OLEFINS USING A FLUOROCARBONSULFONIC ACID POLYMER ON AN INERT SUPPORT

[75] Inventors: John R. Sanderson, Leander; Yu-Hwa Sheu, Austin, both of Tex.

[73] Assignee: Texaco Chemical Company, White Plains, N.Y.

[21] Appl. No.: 597,267

[22] Filed: Oct. 15, 1990

[51] Int. Cl.$^5$ .............................................. C07C 2/74
[52] U.S. Cl. ................................... 585/255; 502/168
[58] Field of Search ................................ 585/255

[56] References Cited

U.S. PATENT DOCUMENTS

| | | | |
|---|---|---|---|
| 2,593,417 | 4/1952 | D'Alelio | 585/406 |
| 2,834,819 | 5/1958 | D'Alelio | 585/406 |
| 3,149,178 | 9/1964 | Hamilton | 585/255 |
| 3,742,082 | 6/1973 | Brennan | 585/255 |
| 4,022,847 | 5/1977 | McClure | 260/671 R |
| 4,038,213 | 7/1977 | McClure et al. | 252/430 |
| 4,056,578 | 11/1977 | McClure et al. | 260/683.47 |
| 4,060,565 | 11/1977 | McClure et al. | 260/671 R |
| 4,065,512 | 12/1977 | Cares | 585/508 |
| 4,065,515 | 12/1977 | McClure et al. | 252/430 |
| 4,180,695 | 12/1979 | McClure | 585/730 |
| 4,367,352 | 1/1983 | Watts, Jr. et al. | 585/254 |
| 4,400,565 | 8/1983 | Darden et al. | 585/10 |
| 4,613,723 | 9/1986 | Olab | 585/458 |
| 4,683,216 | 7/1987 | Farcasieu | 502/159 |
| 4,837,372 | 6/1989 | Zimmerman | 585/514 |
| 4,912,280 | 3/1990 | Clerici | 585/516 |

FOREIGN PATENT DOCUMENTS

0318736 6/1989 European Pat. Off. .

OTHER PUBLICATIONS

Research Disclosure, Jul. 1980, No. 19515.
J. D. Weaver et al., "Supported Fluorocarbonsulfonic Acid Polymer Heterogenous Acid Catalyst," *Catalysis* 1987, pp. 483-489.
Rajadhyaksha and Chaudhari, "Alkylation of Phenol and Pyrocatechol by Isobutyl Using Superacid Catalysts, " *Ind. Eng. Res.*, 26, 1276-1280 (1987).

*Primary Examiner*—Patrick P. Garvin
*Assistant Examiner*—E. D. Irzinski
*Attorney, Agent, or Firm*—Jack H. Park; Kenneth R. Priem; Russell R. Stolle

[57] ABSTRACT

A process is disclosed for preparing synthetic lubricant base stocks having a high dimer to trimer ratio from long-chain olefins. These synthetic lubricant base stocks are prepared in good yield by dimerizing linear olefins using a catalyst comprising a fluorocarbonsulfonic acid polymer on an inert support.

21 Claims, No Drawings

DIMERIZATION OF LONG-CHAIN OLEFINS USING A FLUOROCARBONSULFONIC ACID POLYMER ON AN INERT SUPPORT

BACKGROUND OF THE INVENTION

1. Field of the Invention

The invention relates to the preparation of synthetic lubricant base stocks, and more particularly to synthetic lubricant base stocks made by dimerizing long-chain linear olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Generally, synthetic base stocks are prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, for some applications, such as semi-synthetic oils or where low temperature properties are important, a higher dimer to trimer ratio than that obtained using such conventional oligomerization catalysts is desireable.

A method for dimerizing long-chain olefins using a less hazardous catalyst is taught in co-assigned U.S. Pat. No. 4,367,352 to Watts, Jr. et al., which discloses the use of a perfluorosulfonic acid resin to dimerize long-chain alpha-olefins. At column 3, the '352 Patent teaches that the perfluorosulfonic acid resin produces a high dimer to trimer ratio, and gives an example showing percent dimer and percent trimer in a ratio of about 4.77:1. Applicants have discovered, surprisingly, that a substantially higher dimer/trimer ratio may be obtained by contacting the olefin feed with a catalyst comprising a fluorocarbonsulfonic acid polymer on an inert support. Like the resins of the '352 Patent, the supported fluorocarbonsulfonic acid polymers also are less hazardous and more easily handled than boron triflouride. While supported fluorocarbonsulfonic acid polymers previously have been used in certain hydrocarbon conversion processes (see U.S. Pat. No. 4,038,213), Applicants believe it was heretofor unknown in the art to use these materials to prepare synthetic lubricant base stocks having a very high percentage of dimers. By maintaining a low percentage of trimer and higher oligomers in the reaction product, Applicants are able to obtain base stocks having excellent low temperature properties while using long-chain monomers as feedstock.

SUMMARY OF THE INVENTION

The invention relates to a process for the preparation of synthetic lubricant base stocks having a high dimer to trimer ratio, comprising contacting a linear olefin containing from 10 to 24 carbon atoms with a heterogenous catalyst comprising a fluorocarbonsulfonic acid polymer on an inert support.

DESCRIPTION OF THE PREFERRED EMBODIMENTS

The olefin monomer feed stocks used in the present invention may be selected from compounds comprising (1) alpha-olefins having the formula $R''CH=CH_2$, where $R''$ is an alkyl radical of 8 to 22 carbon atoms, and (2) internal olefins having the formula $RCH=CHR'$, where $R$ and $R'$ are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 14 to 20, inclusive, with an especially preferred range being 15 to 18, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be dimerized in this invention may be obtained by processes well-known to those skilled in the art and are commercially available.

When the olefin feed contacts the catalyst several reactions may occur. Initially, olefin monomer reacts with olefin monomer to form dimers. The dimerization reaction may be represented by the following general equation:

$$2C_mH_{2m} \xrightarrow{\text{catalyst}} C_{2m}H_{4m}$$

where m represents the number of carbon atoms in the monomer. Some of the dimers that are formed then react with additional olefin monomer to form trimers, and so on, though to a much more limited extent than is observed using prior art catalysts. Thus are Applicants able to obtain base stocks with a substantially higher dimer to trimer ratio than may be obtained with prior art catalysts. Generally, each resulting dimer or higher oligomer contains one double bond.

The catalysts used to effect this reaction are fluorocarbon polymers that contain sulfonic acid groups. Generally, they are copolymers of tetrafluoroethylene and fluorinated vinyl ethers, which contain fluorosulfonyl groups. The polymer is converted to the sulfonic acid or sulfonate form by hydrolysis. The repeating structure of a typical fluorocarbonsulfonic acid polymer may be represented as follows:

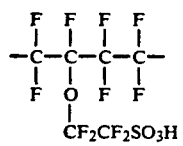

Because the sulfonic acid groups of the fluorocarbonsulfonic acid (FSA) polymers are immersed in a fluorocarbon matrix, many of the acid sites are not accessible to the reactants. As described in the article by J. D. Weaver et al., "Supported Fluorocarbonsulfonic Acid Polymer Heterogenous Acid Catalyst," *Catalysis* 1987, pp. 483 489 (incorporated by reference herein), an effective means of increasing the surface area of the catalyst is to support the polymer as a thin coating on a porous carrier, such as alumina or silicon carbide. Preferred catalysts are Dow Chemical U.S.A.'s fluorocarbonsulfonic acid polymers, designated XUS-40036.01 and XUS-40036.02, which use as the carrier aluminum oxide and silicon carbide, respectively.

The dimerization reaction may be carried out in either a stirred slurry reactor or in a fixed bed continuous flow reactor. The catalyst concentration should be sufficient to provide the desired catalytic effect. The temperatures at which the dimerization may be performed are between about 50 and 200° C., with the preferred range being from about 140 to about 180° C. It is especially preferred that the temperature be about 160° C. The reaction may be run at pressures of from 0 to 1000 psig.

Following the dimerization reaction, the unsaturated dimers, and any higher oligomers present, may be hydrogenated to improve their thermal stability and to guard against oxidative degradation during their use as lubricants. Hydrogenation processes known to those skilled in the art may be used to hydrogenate the dimer-rich bottoms. A number of metal catalysts are suitable for promoting the hydrogenation reaction, including nickel, platinum, palladium, copper, and Raney nickel. These metals may be supported on a variety of porous materials such as kieselguhr, alumina, or charcoal, or they may be formulated into a bulk metal catalyst. A particularly preferred catalyst for this hydrogenation is a nickel-copper-chromia catalyst described in U.S. Pat. No. 3,152,998, incorporated by reference herein. Other U.S. Pats. disclosing known hydrogenation procedures include U.S. Pat. Nos. 4,045,508; 4,013,736; 3,997,622; and 3,997,621.

Unreacted monomer may be removed either prior to or after the hydrogenation step. Optionally, unreacted monomer may be stripped from the reaction products prior to hydrogenation and recycled to the catalyst bed for dimerization. The removal or recycle of unreacted monomer or, if after hydrogenation, the removal of non-dimerized alkane, should be conducted under mild conditions using vacuum distillation procedures known to those skilled in the art. Distillation at temperatures exceeding 250° C. may cause the dimers to break down in some fashion and come off as volatiles. Preferably, therefore, the reboiler or pot temperature should be kept at or under about 225° C. when stripping out the monomer. Procedures known by those skilled in the art to be alternatives to vacuum distillation also may be employed to separate unreacted components from the dimer-rich bottoms product.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention. The entire text of every patent, patent application or other reference mentioned above is hereby incorporated herein by reference.

EXAMPLES

In the examples detailed below, the following procedure was used:

Dimerization of Olefins

Reactants and catalyst were charged to a three-necked flask equipped with an overhead stirrer, thermometer, heating mantle, and a water-cooled condenser ($N_2$ purge). The mixture was vigorously stirred and heated to the desired temperature for the desired time. The mixture was then cooled to ambient temperature and filtered with suction. The liquid was analyzed by liquid chromatography. The results are detailed in Table I.

In order to determine the properties of the resulting lubricant base stocks, several mixtures were reduced (200° C. for 4.0 hours, 2000 psig $H_2$, 5 wt. % nickel catalyst.) The mixture was cooled to ambient temperature after the reaction, the excess hydrogen was vented, and the mixture was filtered from the nickel catalyst. The monomer was "stripped" under vacuum (1.0 mm Hg). The properties are shown in Table II.

TABLE I

DIMERIZATION OF OLEFINS USING FLUOROCARBONSULFONIC ACID POLYMERS ON INERT SUPPORTS

| Ex. No. | Olefin | Catalyst | Wt. % Cat. | Time/Temp (Hr/°C.) | Con. (%) | Dimer/ Trimer + Ratio |
|---|---|---|---|---|---|---|
| 1 | C-14A | XUS40036.02[a] | 10 | 5.0/160 | 73.0 | 13.1 |
| 2 | C-14I8I | " | 10 | 5.0/160 | 47.1 | 16.0 |
| 3 | C-16A | " | 10 | 5.0/160 | 61.3 | 17.7 |
| 4 | C-14A | " | 10 | 5.0/160 | 70.8 | 15.6 |
| 5 | C-14A | XUS40036.01[b] | 10 | 5.0/160 | 76.0 | 13.2 |
| 6 | C-12A | " | 10 | 5.0/140 | 80.9 | 4.47 |
| 7 | C-12A | " | 10 | 5.0/160 | 85.0 | 3.83 |
| 8 | C-12A | " | 10 | 4.0/180 | 75.2 | 3.79 |
| 9 | C-14A | " | 10 | 5.0/160 | 75.7 | 9.87 |
| 10 | C-16A | " | 10 | 5.0/160 | 69.2 | 15.5 |
| 11 | C-15I8I | " | 10 | 5.0/160 | 55.0 | 22.4 |
| 12 | C-12A | XUS40036.02 | 10 | 5.0/140 | 58.0 | 5.93 |
| 13 | C-12A | " | 10 | 5.0/160 | 81.6 | 4.29 |
| 14 | C-12A | " | 10 | 4.0/180 | 80.3 | 5.52 |
| 15 | C-13I4I | " | 10 | 5.0/160 | 79.0 | 8.05 |
| 16 | C-13I4I | XUS40036.01 | 10 | 5.0/160 | 79.7 | 7.13 |

A = Alpha Olefin; I = Internal Olefin; and Con. = Conversion; Trimer + = Trimer + Tetramer + Pentamer, etc.
[a]Dow Chemical U.S.A. Superacid Catalyst: fluorocarbonsulfonic acid polymer on silicon carbide;
[b]Dow Chemical U.S.A. Superacid Catalyst: fluorocarbonsulfonic acid polymer on aluminum oxide.

TABLE II

| | PROPERTIES OF REDUCED DIMER-RICH BOTTOMS | | | | |
|---|---|---|---|---|---|
| Ex. No. | Viscosity @ 210° F. (cSt) | TGA - % Remaining @ 250° C. | Noack Volatility @ 250° C. (%) | Viscosity Index | Pour Point (°F.) |
| 4 | 4.09 | 75.0 | 25.5 | 93 | <−50 |
| 9 | 4.07 | 75.4 | 23.9 | 92 | <−50 |

TGA = Thermogravimetric Analysis

We claim:

1. A process for the preparation of synthetic lubricant base stocks having a high dimer to trimer ratio, comprising contacting a linear olefin containing from 10 to 24 carbon atoms with a heterogenous catalyst comprising a fluorocarbonsulfonic acid polymer on an inert support.

2. The process of claim 1, wherein the fluorocarbonsulfonic acid polymer has the following repeating structure:

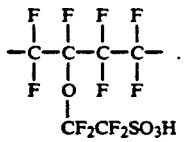

3. The process of claim 1, wherein the inert support is selected from the group consisting of silicon carbide and aluminum oxide.

4. The process of claim 1, wherein the linear olefin contains from 15 to 18 carbon atoms.

5. The process of claim 1, wherein the linear olefin contains 16 carbon atoms.

6. The process of claim 1, wherein the olefin is contacted with the catalyst at a temperature of about 140 to about 180° C.

7. The process of claim 1, wherein the olefin is contacted with the catalyst at a temperature of about 160° C.

8. A process for the preparation of synthetic lubricant base stocks having a high dimer to trimer ratio, comprising contacting a linear olefin containing from 14 to 24 carbon atoms with a fluorocarbonsulfonic acid polymer having the following repeating structure:

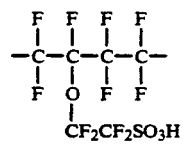

wherein the fluorocarbonsulfonic acid is present as a coating on an inert support, and recovering a bottoms product having a dimer to trimer ratio of about 5:1 or greater.

9. The process of claim 8, wherein the inert support is selected from the group consisting of silicon carbide and aluminum oxide.

10. The process of claim 8, wherein the linear olefin contains from 15 to 18 carbon atoms.

11. The process of claim 8, wherein the linear olefin contains 16 carbon atoms.

12. The process of claim 8, wherein the olefin is contacted with the fluorocarbonsulfonic acid polymer at a temperature of about 140 to about 180° C.

13. The process of claim 8, wherein the olefin is contacted with the fluorocarbonsulfonic acid polymer at a temperature of about 160° C.

14. The process of claim 8, wherein the base stock recovered has a dimer to trimer ratio of about 10:1 or greater.

15. The process of claim 8, wherein the base stock has a dimer to trimer ratio of about 15:1 or greater.

16. A process for the preparation of a synthetic lubricant base stock having a high dimer to trimer ratio, comprising the following steps: (a) contacting a linear olefin containing from 14 to 24 carbon atoms with a catalyst comprising a fluorocarbonsulfonic acid polymer having the following repeating structure:

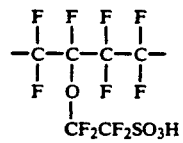

wherein the fluorocarbonsulfonic acid is present as a coating on an inert support, and wherein the catalyst and olefin are contacted at a temperature of about 140 to about 180° C.; (b) separating out any remaining unreacted olefin to recover a synthetic lubricant base stock having a dimer to trimer ratio of about 5:1 or greater; and (c) hydrogenating the base stock resulting from step (b).

17. The process of claim 16, wherein the inert support is selected from the group consisting of silicon carbide and aluminum oxide.

18. The process of claim 16, wherein the linear olefin contains from 15 to 18 carbon atoms.

19. The process of claim 16, wherein the linear olefin contains 16 carbon atoms.

20. The process of claim 16, wherein the olefin is contacted with the catalyst at a temperature of about 160° C.

21. The process of claim 16, wherein the base stock recovered has a dimer to trimer ratio of about 10:1 or greater.

* * * * *